United States Patent
Patil et al.

(10) Patent No.: US 11,967,421 B2
(45) Date of Patent: Apr. 23, 2024

(54) SELF-CORRECTING METHOD FOR ANNOTATION OF DATA POOL USING FEEDBACK MECHANISM

(71) Applicant: KONINKLIJKE PHILIPS N.V., Eindhoven (NL)

(72) Inventors: Ravindra Balasaheb Patil, Bangalore (IN); Meru Adagouda Patil, Bangalore (IN); Sarif Kumar Naik, Bangalore (IN); Vidya Ravi, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 856 days.

(21) Appl. No.: 16/981,331

(22) PCT Filed: Mar. 6, 2019

(86) PCT No.: PCT/EP2019/055526
§ 371 (c)(1),
(2) Date: Sep. 16, 2020

(87) PCT Pub. No.: WO2019/179765
PCT Pub. Date: Sep. 26, 2019

(65) Prior Publication Data
US 2021/0012891 A1    Jan. 14, 2021

Related U.S. Application Data (60) Provisional application No. 62/646,993, filed on Mar. 23, 2018.

(51) Int. Cl.
| | |
|---|---|
| *G16H 40/40* | (2018.01) |
| *G06F 11/30* | (2006.01) |
| *G06F 40/205* | (2020.01) |
| *G06F 40/211* | (2020.01) |
| *G06N 5/025* | (2023.01) |
| *G06N 5/04* | (2023.01) |
| *G16H 30/00* | (2018.01) |

(52) U.S. Cl.
CPC ............ *G16H 40/40* (2018.01); *G06F 11/30* (2013.01); *G06F 40/205* (2020.01);
(Continued)

(58) Field of Classification Search
CPC ...... G16H 40/40; G16H 30/00; G06F 40/211; G06F 40/205; G06F 11/30; G06N 5/025; G06N 5/04
See application file for complete search history.

(56) References Cited

U.S. PATENT DOCUMENTS 4,853,946 A * 8/1989 Elliott ................. H05G 1/54
378/207
5,463,768 A   10/1995 Chuddihy
(Continued)

FOREIGN PATENT DOCUMENTS

| WO | 2012/037429 | 3/2012 |
| WO | 2014/043623 | 3/2014 |

OTHER PUBLICATIONS

International Search Report and Written Opinion dated Jun. 13, 2019 for International Application No. PCT/EP2019/055526 Filed Mar. 6, 2019.
(Continued)

*Primary Examiner* — Beau D Spratt (57) ABSTRACT

In a monitoring method for generating maintenance alerts, component IDs are extracted which identify medical imaging device components in electronic medical imaging device manuals (25, 26, 27, 28). Operating parameters of the medical imaging device components and associated operating parameter ranges are also extracted from the manuals, based on numeric values, parameter terms identifying operating parameters, and linking terms or symbols indicative of equality or inequality that connect the numeric values and parameter terms. The operating parameter ranges are formulated into decision rules (36) which are applied to log
(Continued)

| Component | Parameter : values | Rules |
|---|---|---|
| Dedicated distribution transformer | Power rating : 225 kVA | Check power rating |
| | Regulation at unity power factor (p.f.) : 2.4% | Check if regulation at 1 p.f. = 2.5% |
| | Maximum feeder regulation : 3.4% | Check if max feeder regulation <= 3.4% |
| | Maximum power demand at 0.85 p.f. : 105 kVA | Check if max power demand at 0.85 p.f. is <= 150 kVA |
| | Maximum total source regulation : 6% | Check if max (total source regulation) <= 6% | data (40) generated by a monitored medical imaging device (2) to detect out-of-range log data generated by the monitored medical imaging device. Maintenance alerts (24) are displayed on a display (18) in response to the detected out-of-range log data. The maintenance alerts are generated from out-of-range log data and are associated with component IDs contained in the out-of-range log data.

17 Claims, 9 Drawing Sheets (52) U.S. Cl.
CPC ........... *G06F 40/211* (2020.01); *G06N 5/025* (2013.01); *G06N 5/04* (2013.01); *G16H 30/00* (2018.01)

(56) References Cited

U.S. PATENT DOCUMENTS

| | | | |
|---|---|---|---|
| 6,442,542 B1 | 8/2002 | Ramani | |
| 6,598,179 B1 | 7/2003 | Chirashyna | |
| 6,650,949 B1 | 11/2003 | Fera | |
| 7,260,249 B2 * | 8/2007 | Smith | G16H 30/40 382/128 |
| 9,552,249 B1 | 1/2017 | James | |
| 2008/0222070 A1 * | 9/2008 | Damodharan | G06F 11/2257 706/47 |
| 2009/0089237 A1 * | 4/2009 | Hebbar | G06N 5/025 706/50 |
| 2014/0046697 A1 * | 2/2014 | Rogers | G16H 10/60 705/3 |
| 2014/0266713 A1 * | 9/2014 | Sehgal | G16H 40/40 340/540 |
| 2014/0343957 A1 * | 11/2014 | Dejori | G16H 50/70 705/2 |
| 2014/0365828 A1 | 12/2014 | Jiang | |
| 2015/0089309 A1 | 3/2015 | Fu | |
| 2016/0306691 A1 * | 10/2016 | Aneja | G06F 11/0709 |

OTHER PUBLICATIONS

Allahyari et al: "A Brief Survey of Text Mining: Classification, Clustering and Extraction Techniques", arxiv.org, Cornell University Library, 201, Olin Library Cornell University Ithaca, NY 14853, Jul. 10, 2017.

* cited by examiner

FIG. 1

"Dedicated distribution transformer

It is recommended a dedicated (feeder) distribution transformer (from the facility's main isolation transformer) supply power to the CT scanner.

The minimum recommended size for a dedicated distribution transformer is: 225 kVA, rated 2.4% regulation at unity power factor. Resultant maximum allowable feeder regulation is 3.4%.

Do not use an existing distribution transformer to power a system if other X-ray equipment, using rapid film changers, is connected to the existing transformer.

System power requirements

The customer shall ensure the site meets all minimum system power requirements listed below before installation can begin

FIG. 2

| Component | Key metrics |
|---|---|
| Dedicated distribution transformer | dedicated distribution transformer is : 225 kVA, rated |
| | 2.4% regulation at unity power factor. |
| | Resultant maximum allowable feeder regulation is 3.4%. |
| | Maximum power demand = 150 kVA @ 0.85 PF ; |
| | Maximum allowable total source regulation is 6%." |

| | | | | | | | | | | | | | |
|---|---|---|---|---|---|---|---|---|---|---|---|---|---|
| | Component 1 | $V_1$ | $V_1$ | | | | | | | | | | |
| $P_1$ | Param 1 | $V_1$ | $V_1$ | | | | | | | Vk1 | | | |
| $P_2$ | Param 2 | $V_1$ | $V_1$ | $V_3$ | | | | | Vk2 | | | | |
| $P_3$ | Param 3 | $V_1$ | $V_1$ | $V_3$ | | | | | | Vk3 | | | |
| $P_4$ | Param 4 | $V_1$ | $V_1$ | $V_3$ | | | Vk4 | | | | | | |
| | Component 2 | | | | | | | | | | | | |
| $P_5$ | Param 1 | $V_1$ | $V_1$ | | | Vk5 | | Vk6 | | | | | |
| $P_6$ | Param 2 | $V_1$ | $V_1$ | $V_3$ | | | | | | | | | |
| | Component 3 | | | | | | | | | | | | |
| $P_7$ | Param 1 | $V_1$ | $V_1$ | | | | | | | | Vk7 | | |
| $P_8$ | Param 2 | $V_1$ | $V_1$ | $V_3$ | | | | | | | | Vk8 | |
| $P_9$ | Param 3 | $V_1$ | $V_1$ | $V_3$ | | | | | | | | | Vk9 |
| $P_{10}$ | Param 4 | $V_1$ | $V_1$ | $V_3$ | V10 | | | | | | | | |

FIG. 5

| Component | Parameter : values | Rules |
|---|---|---|
| Dedicated distribution transformer | Power rating : 225 kVA | Check power rating |
| | Regulation at unity power factor (p.f.) : 2.4% | Check if regulation at 1 p.f. = 2.5% |
| | Maximum feeder regulation : 3.4% | Check if max feeder regulation <= 3.4% |
| | Maximum power demand at 0.85 p.f. : 105 kVA | Check if max power demand at 0.85 p.f. is <= 150 kVA |
| | Maximum total source regulation : 6% | Check if max (total source regulation) <= 6% |

SELF-CORRECTING METHOD FOR ANNOTATION OF DATA POOL USING FEEDBACK MECHANISM

CROSS REFERENCE TO RELATED APPLICATIONS

This application is the U.S. National Phase application under 35 U.S.C. § 371 of International Application No. PCT/EP2019/055526 filed Mar. 6, 2019, which claims the benefit of U.S. Provisional Patent Application No. 62/646,993 filed Mar. 23, 2018. These applications are hereby incorporated by reference herein.

FIELD

The following relates generally to the medical imaging device maintenance arts, device monitoring arts, predictive maintenance arts, and related arts.

BACKGROUND

Medical devices used in the healthcare industry, such as magnetic resonance imaging (MRI) scanners, computed tomography (CT) scanners, positron emission tomography (PET) scanners, gamma cameras used in single photon emission computed tomography (SPECT), image-guided therapy (iGT) systems, and other medical imaging devices, or electrocardiograph (ECG) or patient monitor devices, and so forth, should be in good working condition to ensure doctors and patients receive correct information for medical diagnoses and patient monitoring and so forth. Medical imaging devices are expensive to replace and play a crucial role in diagnosis. Any downtime of these devices results in a loss of revenue to the medical institution, loss of quality treatment for patients, and introduces delays into patient treatment. Emphasis is thus placed on minimizing the downtime of medical imaging devices and ensuring uninterrupted operational status while maintaining quality of performance.

Predictive maintenance is an important part of minimizing downtime of medical imaging devices. This approach entails predicting and proactively repairing or otherwise remediating possible failures of medical imaging device components in advance based on the machine logs and usage history. In this way, maintenance can be proactively performed to minimize or eliminate downtime and impact on patient care.

However, predictive maintenance is difficult to implement in practice. Modern medical imaging devices produce huge volumes of log data, on the order of gigabytes or terabytes or higher. Furthermore, proactively identifying log data that statistically indicates a likely component failure is difficult due to the time lag between the log data and the subsequent component failure. Still further, determining which log data is useful in predicting a component failure is difficult. Conventionally, prior information has been used to identify these types of bad log data indicative of a likely component failure. The prior information is typically provided by subject matter experts with specialized technical knowledge of the medical imaging device components, their performance envelopes and the possible problems. Generation of the knowledge engine for performing predictive maintenance is typically a laborious process requiring input of subject matter experts knowledgeable in the medical imaging devices and their components to develop decision rules that can be applied to log data of a monitored medical imaging device.

A further problem is that the resulting predictive maintenance system is static. This is a problem because medical imaging device manufacturers are continually adding new products and improving existing product lines. These changes will not be reflected in the knowledge engine used for predictive maintenance. Consequently, manual updating of the knowledge engine must be performed on a frequent basis, which again requires extensive input from subject matter experts.

The following discloses certain improvements.

SUMMARY

In some embodiments disclosed herein, a non-transitory storage medium stores instructions readable and executable by an electronic processor to perform a monitoring method for generating maintenance alerts. The monitoring method includes: extracting component identifications (component IDs) identifying medical imaging device components and operating parameters of the identified medical imaging device components and associated operating parameter ranges from electronic medical imaging device manuals; generating a knowledge engine by operations including formulating the operating parameter ranges into a set of decision rules for classifying medical imaging device log data; and applying the knowledge engine to log data generated by a monitored medical imaging device to detect out-of-range log data generated by the monitored medical imaging device and to generate maintenance alerts in response to the detected out-of-range log data wherein the maintenance alerts are associated with component IDs contained in the detected out-of-range log data.

In some embodiments disclosed herein, a monitoring device is disclosed for generating maintenance alerts. The monitoring device comprises a display, a non-transitory storage medium as set forth in the immediately preceding paragraph, and an electronic processor operatively connected with the display and with the non-transitory storage medium to perform the monitoring method further including displaying the generated maintenance alerts on the display.

In some embodiments disclosed herein, a monitoring method performed by an electronic processor is disclosed for generating maintenance alerts. Component identifications (component IDs) are extracted which identify medical imaging device components in electronic medical imaging device manuals. Operating parameters of the identified medical imaging device components and associated operating parameter ranges are extracted from the electronic medical imaging device manuals based on numeric values, parameter terms identifying operating parameters, and linking terms or symbols indicative of equality or inequality that connect the numeric values and parameter terms. The operating parameter ranges are formulated into decision rules for classifying medical imaging device log data based on whether a value of the associated operating parameter is outside of the operating parameter range. The decision rules are applied to log data generated by a monitored medical imaging device to detect out-of-range log data generated by the monitored medical imaging device, and maintenance alerts are displayed on a display in response to the detected out-of-range log data. The maintenance alerts are generated from out-of-range log data and are associated with component IDs contained in the out-of-range log data.

In some embodiments disclosed herein, a monitoring device is disclosed for generating maintenance alerts. The monitoring device includes a display, an electronic processor operatively connected with the display, and a non-transitory storage medium storing instructions readable and executable by the electronic processor to perform a monitoring method for generating maintenance alerts. In the monitoring method, decision rules are generated for classifying medical imaging device log data based on whether parameter values of operating parameters of medical imaging device components identified by component identifications (component IDs) in the log data are within operating parameter ranges for the respective operating parameters. The operating parameter ranges for the respective operating parameters are extracted from electronic medical imaging device manuals. The decision rules are applied to log data generated by a monitored medical imaging device to detect out-of-range log data generated by the monitored medical imaging device. The display is controlled to present maintenance alerts in response to the detected out-of-range log data wherein the maintenance alerts are associated with component IDs contained in the detected out-of-range log data.

One advantage resides in providing a monitoring device for generating maintenance alerts for one or more monitored medical imaging devices, in which the knowledge engine of the monitoring device is generated automatically.

Another advantage resides in providing such a monitoring device in which the knowledge base is continuously and efficiently updated based on service logs of the monitored medical imaging devices.

Another advantage resides in providing such a monitoring device with computationally efficient generation and updating of the knowledge base.

Another advantage resides in providing such a monitoring device in which the knowledge base is developed without input from subject matter experts.

Other advantages include reduced total time to build predictive models, elimination of subjectivity in labeling hence reducing manual error, and auto feedback for re-learning and self-correcting decision rules used for generating maintenance alerts.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

In embodiments disclosed herein, electronic medical imaging device manuals are leveraged to extract component identifications (component IDs) identifying medical imaging device components and operating parameters of the identified medical imaging device components and associated operating parameter ranges. The electronic medical imaging device manuals can take substantially any machine-readable form, and may be online manuals, printed manuals that are scanned to pdf (or another electronic format) and processed by optical character recognition (OCR) to generate machine-readable text, and/or so forth. The electronic medical imaging device manuals may, for example, include one or more of a service manual, manufacturer specification(s), a user manual, an operating reference manual, and/or so forth. A knowledge engine is then generated by operations including formulating the operating parameter ranges into a set of decision rules for classifying medical imaging device log data. For example, a decision rule may classify input log data as bad (i.e. out-of-range) log data if the input log data indicates a value for an operating parameter that is outside of the operating parameter range associated with that operating parameter. The knowledge engine is then applied to log data generated by a monitored medical imaging device to detect out-of-range log data generated by the monitored medical imaging device and to generate maintenance alerts in response to the detected out-of-range log data. The maintenance alerts are suitably associated with component IDs contained in the detected out-of-range log data, and may in some embodiments be formulated as maintenance recommendations. For example, if the temperature of a component is indicated as being outside of the operating temperature range for that component, then the alert may be formulated as "<Component ID> operating temperature may be above its recommended operating temperature. Recommend to check temperature of <Component ID>."

A further aspect is that accuracy of the generated maintenance alerts may be determined based on feedback extracted from a service log of the monitored medical imaging device, and the knowledge engine may be updated by adjusting the decision rules based on the determined accuracy of the generated maintenance alerts. For example, accuracy of a generated maintenance alert may be determined based on feedback extracted from the service log over a time interval extending from a time of generation of the maintenance alert to an end time which is dependent upon (and may be equal to) the mean time to failure (MTTF) of the medical imaging device component identified by the component ID associated with the maintenance alert.

By the disclosed approaches, the need for manual development and curation of a set of decision rules for performing predictive maintenance is reduced or eliminated.

Figure 1:
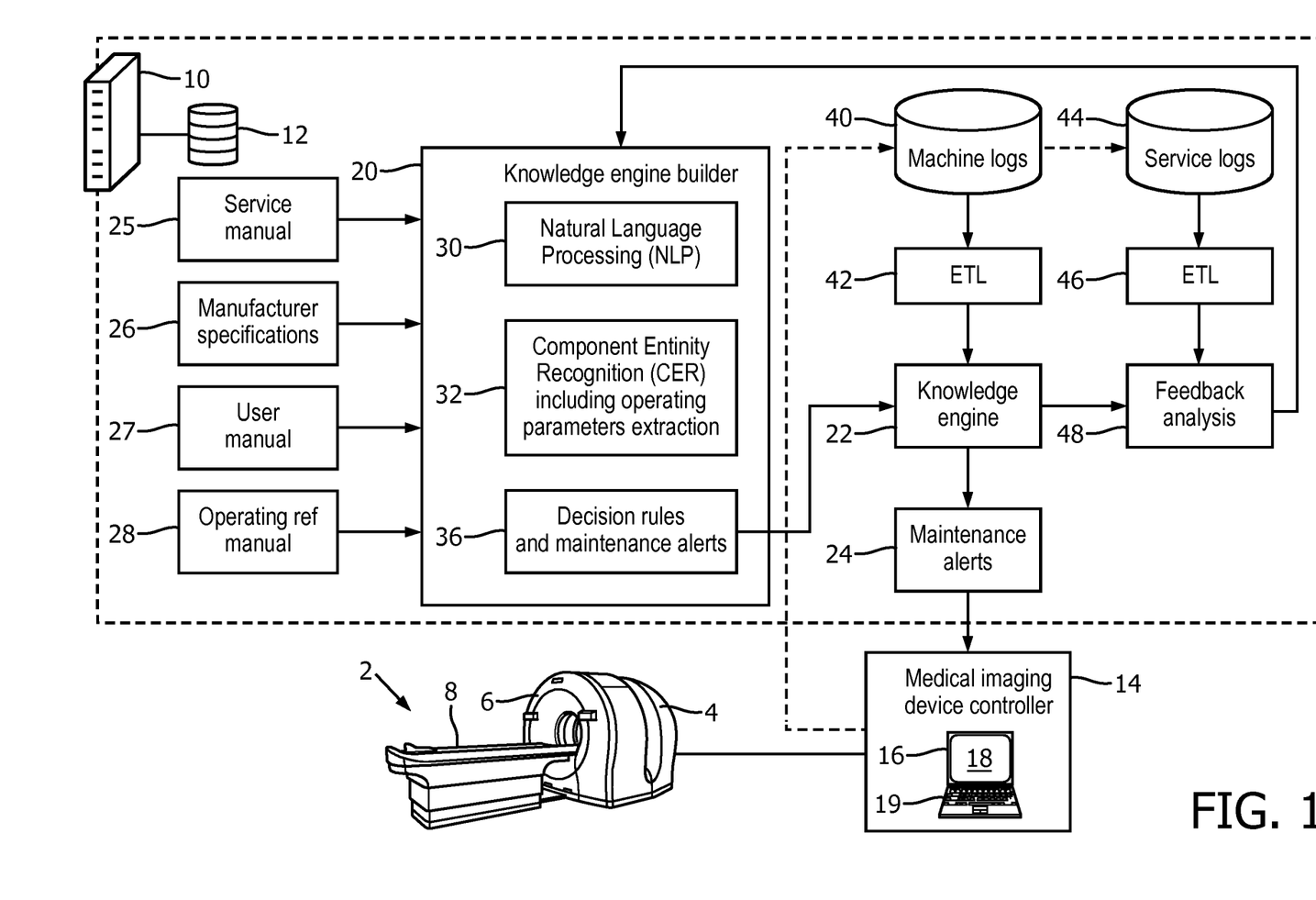
FIG. 1 diagrammatically illustrates a monitoring device for performing predictive maintenance including generating maintenance alerts for a monitored medical imaging device based on log data generated by the monitored medical imaging device, in which decision rules for generating the maintenance alerts are automatically generating.

With reference to FIG. 1, a monitoring device is disclosed for generating maintenance alerts for a medical imaging device 2. The illustrative medical imaging device 2 is a PET/CT scanner including a positron emission tomography (PET) gantry 4 and a transmission computed tomography (CT) gantry 6 positioned in-line such that a patient can be loaded into either gantry 4, 6 via a common robotic patient support or couch 8. Such a PET/CT scanner 2 is commonly used in numerous diagnostic and clinical tasks (e.g. oncology, cardiology, neurology, and so forth) as the CT imaging performed by the CT gantry 6 provides anatomical information that is complementary to functional information provided by PET imaging performed by the EPT gantry 4. As just one illustration of this synergy, a CT image can be used to generate an attenuation map that is used to perform attenuation correction during PET image reconstruction. The PET/CT scanner 2 is a highly complex medical imaging device with thousands of components, e.g. as a very few non-limiting examples including dozens or hundreds of PET detector modules, an X-ray tube and dozens or hundreds of X-ray detector modules (components of the CT gantry 6), mechanical components for revolving the X-ray tube and X-ray detector array around the patient, numerous robotic mechanisms of the patient support or couch 8, electrical power components such as a distribution transformer for delivering electrical power to the PET/CT 2, and so forth (note, detailed medical imaging device components are not illustrated in FIG. 1). Each component typically has one, two, three, or more operating parameters that are monitored by appropriate sensors. For example, each PET detector module may include a temperature sensor that outputs module operating temperature, electrical sensors that monitor dark current and/or other electrical operating parameters, and/or so forth. A robotic component of the couch 8 may include position encoders that monitor positioning of a robotic actuator. The CT gantry may include sensors monitoring rotation speed and encoding rotational angular position. The distribution transformer may include sensors monitoring operating power factor, input and output voltage, and so forth. Again, these are merely a few non-limiting illustrative examples. While the illustrative monitored medical imaging device 2 is a PET/CT scanner, it will be appreciated that the monitored medical imaging device may more generally be any type of medical imaging device with sufficient complexity to justify continuous monitoring and generation of timely maintenance alerts as disclosed herein. For example, the monitored medical imaging device may be a PET/CT scanner, a SPECT/CT scanner, a standalone gamma camera, standalone PET scanner, standalone CT scanner, an magnetic resonance (MR) imaging scanner, a PET/MR scanner, an image-guided therapy (iGT) device, or so forth. Moreover, it will be appreciated that the disclosed predictive maintenance monitoring devices and methods may be applied to monitor many such medical imaging devices, possibly of different types, in parallel.

With continuing reference to FIG. 1, the illustrative monitoring device includes a server computer 10 or other electronic processor (e.g. desktop computer with sufficient computing capacity) operatively connected with a non-transitory storage medium 12 that stores instructions that are readable and executable by the electronic processor 10 to perform a monitoring method as disclosed herein, and a monitor interface device 14 which, in the illustrative embodiment, is embodied by a computer 16 that serves as a medical imaging device controller 14 for controlling the monitored medical imaging device 2 (e.g., to operate the robotic support 8 to load a patient into the appropriate gantry, to select and execute an imaging sequence or protocol, to perform reconstruction of the acquired imaging data to generate an image and to display the image on a display 18 of the computer, and/or so forth). In other embodiments, the monitor interface device may be a separate computer, or may be integral with the computer 10 that performs the monitoring method. The monitor interface device includes the display 18 for presenting maintenance alerts or other information, and may optionally include one or more user input devices (e.g. illustrative keyboard 19) for receiving user inputs.

The non-transitory storage medium 12 may be variously embodied, e.g. as a hard disk drive, RAID array, or other magnetic storage medium, a solid state drive (SSD) or other electronic storage medium, an optical disk or other optical storage medium, various combinations thereof, and/or so forth. Further, it will be appreciated that the illustrative electronic processors 10, 16 may be otherwise variously embodied and/or combined, and/or the various non-transitory storage media may be variously embodied, e.g. by way of linkages via electronic data networks or the like. For example, the electronic processor 10 may be implemented as a cloud computing resource comprising an ad hoc combination of a number of server computers.

The electronic processor 10 reads and executes instructions stored on the non-transitory storage medium 12 in order to perform a monitoring method including implementing a knowledge engine builder 20 that builds, and optionally subsequently adaptively maintains or updates, a knowledge engine 22 comprising a set of decision rules for generating maintenance alerts 24. To this end, the knowledge engine builder 20 leverages inputs from available electronic medical imaging device operating data. A commonly available form of electronic medical imaging device servicing and operating data are electronic manuals, such as an illustrative service manual 25, an illustrative set of manufacturer's specifications 26, an illustrative user manual 27, and an illustrative operating reference manual 28. These are merely illustrative titles, and it will be appreciated that various medical imaging device manufacturers and users (e.g. hospitals) may employ different titling for the electronic medical imaging device manuals. Likewise, the manual content may be variously distributed amongst one or more such manuals, e.g. in some implementations a single manual may cover the combined content of the illustrative user manual 27 and operating reference manual 28, and/or the service manual may include the manufacturer's specifications as one or more appendices of the service manual, rather than as a separate manufacturer's specifications document, and/or so forth. The electronic medical imaging device servicing and operating data may also include service notes compiled into electronic form (e.g. electronic service logs maintained by service engineers), updates to the manuals (e.g. base system parameter updates, or upgraded operating parameters due to system/software upgrades, and/or so forth), external data such as online servicing and operating data available at the medical imaging device vendor's website, and/or so forth. The various electronic medical imaging device servicing and operating data 25, 26, 27, 28 are preferably specific to the make and model of the medical imaging device 2 to be monitored, although such a requirement may be relaxed in instances in which different makes and/or models of a particular type of medical imaging device share certain systems or sub-systems.

The knowledge engine builder 20 processes the content of the electronic medical imaging device servicing and operating data 25, 26, 27, 28 to extract component identifications (component IDs) identifying medical imaging device components, and to extract operating parameters of the identified components, and to extract operating parameter ranges associated with the respective operating parameters. To this end, the manuals are assumed to be in electronic form with machine readable text. (If this is not initially the case, then optical scanning, photocopying, photography, or the like can be employed to generate digital images of the manual pages, followed by OCR, to covert a paper manual into electronic format with machine-readable text). Natural language processing (NLP) 30 is performed on text of the electronic medical imaging device servicing and operating data 25, 26, 27, 28 to tokenize the text into individual tokens (e.g. words), remove uninformative common words (e.g. "the", "a", et cetera), perform word stemming and lemmatization, and/or so forth. The NLP 30 may include parsing of text and tables of the electronic medical imaging device manuals to delineate semantic units including sentences, paragraphs, list items, table rows, or so forth.

Component entity recognition (CER) 32 is applied to identify component IDs in the NLP-processed text that identify medical imaging device components. The CER 32 may employ any type of named entity recognition (NER) algorithm or combination of NER algorithms, e.g. leveraging a domain-specific vocabulary list to identify component IDs, identifying component IDs based on factors such as part-of-speech (if the NLP 30 includes grammatical parsing), and/or so forth. Although the CER 32 is preferably a fully automated process, in alternative embodiments it is contemplated to be semi-supervised, e.g. with uncertain component IDs presented to a user for confirmation or rejection. The CER 32 also performs operating parameters extraction to extract operating parameters of the medical imaging device components identified by component IDs, along with associated operating parameter ranges. In one approach, operating parameters are identified by identifying numeric values and parameter terms which are connected by linking terms or symbols indicative of equality or inequality, and associating parameters identified by the parameter terms with medical imaging device components whose component IDs occur in the same semantic units as the parameter terms. For example, the sentence: "The PET detector modules should be kept at a temperature below 100° C." can be processed by identifying the numeric value (100° C.) and a parameter term (temperature) which are connected by a linking term or symbol indicative of equality or inequality (below), and the operating parameter "temperature" is associated with the component ID (PET detector) occurring in the same semantic unit (same sentence) as the parameter term (temperature). Parameter terms can be identified using NER to identify "named entities" representing operating parameters, e.g. using a domain-specific vocabulary list, part-of-speech (if grammatical parsing if available), and/or so forth. Again, this is preferably a fully automated approach but in some embodiments semi-supervised parameter term extraction is contemplated, e.g. by presenting uncertain parameter names to a user for confirmation or rejection. Operating parameter ranges associated with operating parameters are determined based on the numeric values and the equalities or inequalities indicated by the linking terms or symbols. In the last example, the extracted operating range for the operating parameter "temperature" of the component ID "PET detector" can be expressed as "temperature<100° C.". The knowledge engine 22 is then generated by operations including formulating the operating parameter ranges into a set of decision rules 36 for classifying medical imaging device log data as good data (e.g. within operating range) or bad log data (e.g. outside operating range). Advantageously, the extraction of component IDs and operating parameters and associated operating parameter ranges, and the generating of the knowledge engine 22, does not require receiving input from a subject matter expert.

Monitoring of the monitored medical imaging device 2 leverages machine logs 40 which are commonly generated by medical imaging devices. In illustrative FIG. 1, the machine logs are generated by the medical imaging device controller 14 based on readings of the various sensors of the components, sub-systems, and systems of the monitored medical imaging device 2. The machine logs 40 may be stored on the non-transitory storage medium 12 using a logging format that typically employs a standardized syntax and formatting for the machine type and manufacturer of the medical imaging device 2. Consequently, extract-transform-load (ETL) 42 of the machine log data 40 is straightforward based on the known standard log notation. Component IDs and operating parameters and their logged values are identified in the ETL-processed log data, and the knowledge engine 22 applies the decision rules 36 to this information to identify any operating parameters whose values are out of the corresponding operating parameter range. Identified out-of-range operating parameters trigger the generation of maintenance alerts 24. Said another way, the knowledge engine 22 is applied to the log data generated by the monitored medical imaging device 2 to detect bad log data generated by the monitored medical imaging device 2 and to generate maintenance alerts 24 in response to the detected bad log data. The maintenance alerts are associated with component IDs contained in the detected bad log data, e.g. the log data will report a temperature reading being associated with the component (identified by its component ID) for which the reading was taken. Optionally, the generation of a maintenance alert may occur only after the out-of-range parameter value is detected for a certain time interval (possibly sensor-dependent) to avoid overaggressive triggering of maintenance alerts by occasional inaccurate sensor readings. It is also contemplated for maintenance alerts 24 to be coupled with out-of-range log data (or more specifically, out-of-range parameter values of the log data) on other than a 1:1 basis. A maintenance alert 24 may be generated in response to a detected combination of two or more parameters that are outside their respective operating parameter ranges in the out-of-range log data. That is, a decision rule may be applied to detect a combination of two or more parameters that are outside their respective operating parameter ranges in the out-of-range log data. For example, a maintenance alert could be generated in response to a (possibly weighted) sum of different out-of-range parameters, e.g. if two parameters might be out-of-range by amounts that individually would not trigger a maintenance alert, but the combination of out-of-range parameters may trigger an alert. The alert may be triggered at lower tolerances, e.g. considering parameters identified generically as parameters A and B, a maintenance alert may be issued if: A>5%; B>10% or A>3% AND B>8%. In this example, the tolerance of parameter A is weighted higher than that of parameter B (40% v. 20% in the combination tolerance change).

The maintenance alerts 24 are presented to the user, e.g. by being displayed in an "alerts" window shown on the display 18 of the monitor interface device 14. For example, a maintenance alert may be presented as a maintenance recommendation, e.g. "Recommend to check PET detector temperature, recent readings have exceeded the recommended upper limit of 100° C." In some embodiments, the maintenance alerts may be graded as to severity or urgency, e.g. based on how far out-of-range the parameter value is (e.g., a PET detector reading of 102° C. may trigger a lowest-level alert while a reading of 115° C. may trigger a higher-level alert), and/or based on the criticality of the component (e.g. an out-of-range parameter reading for the PET detectors may generate a higher-level alert than an out-of-parameter reading for a bearing of the patient support 8). In some embodiments, the processing 30, 32 of the manuals may include detection of urgency notations contained in the text of the manuals themselves. For example, it is not uncommon for a manual to highlight critical parameter ranges by keywords such as "IMPORTANT"—when such a keyword is detected in conjunction with an extracted decision rule then this decision rule may be tagged as being of high importance, and any maintenance alert triggered by such a rule will be assigned a high alert level. The maintenance alerts 24 may optionally also indicate severity or urgency in other terms, such as by the potential impact (e.g. slow performance, short-term breakdown, long-term breakdown, potential clinical impact, and/or so forth). In addition to being presented to the user, the maintenance alerts 24 may optionally also be forwarded to the medical imaging device vendor or other maintenance service provider to potentially align service calls and/or parts distribution.

In some embodiments, feedback from the logs is used to adaptively adjust or tune the decision rules 36 applied by the knowledge engine 22. This leverages service logs 44 which are typically maintained for the medical imaging device 2, e.g. based on service records generated manually by service personnel and/or automatically by system software that, for example, detects and timestamps replacement of various components. The service logs 40 may be stored on the non-transitory storage medium 12 using a logging format that typically employs a standardized syntax and formatting for the machine type and manufacturer, and/or a standardized syntax and formatting used by the servicing organization. Consequently, ETL 46 of the service log data 44 is straightforward based on the known standard log notation. In general, accuracy of generated maintenance alerts 24 is determined in a feedback analysis 48 based on feedback extracted from the service log 44, and the knowledge engine 22 is updated by adjusting the decision rules 36 based on the determined accuracy of the generated maintenance alerts. For example, accuracy of a generated maintenance alert may be determined based on feedback extracted from the service log 44 over a time interval extending from a time of generation of the maintenance alert to an end time that is dependent upon a mean time to failure (MTTF) of the medical imaging device component identified by the component ID associated with the maintenance alert. To account for statistical variability, the end time may be a scaled value, e.g. 1.5×MTTF. If servicing of the subject component is recorded in the service log 44 during this time interval, or if a failure of the subject component is recorded in the service log 44, then the maintenance alert may be deemed to be accurate. On the other hand, if no servicing is detected in this time interval and the subject component does not fail, then it may be assumed that the maintenance alert was not accurate, in that service personnel did not believe it appropriate to act upon the maintenance alert and indeed the maintenance alert did not accurately predict an impending failure of the subject component.

If the feedback analysis 48 determines that the maintenance alert was accurate, then no adaptation or remediation is performed. On the other hand, if the feedback analysis 48 determines that the maintenance alert was not accurate, then this information is used to adjust or remediate the decision rule that triggered the maintenance alert. In preferred fully automated adaptation embodiments, the adjustment or remediation of the inaccurate decision rule may entail removal of the inaccurate decision rule, or adjustment of the operating parameter range of the inaccurate decision rule. Such adjustment may employ a percentage change, for example if the inaccurate decision rule triggers a maintenance alert if a maximum parameter value threshold is exceeded, then this threshold may be increased by 5% (or by 10%, or by some other chosen adjustment increment). Likewise, if the inaccurate decision rule triggers a maintenance alert if a minimum parameter value threshold is exceeded, then this threshold may be decreased by 5% (or by 10%, or by some other chosen adjustment increment). In a variant semi-supervised embodiment, the inaccurate decision rule may be presented to a user for review, perhaps along with instances in which it has triggered alerts in the past, and the user may elect to make a manual adjustment to the inaccurate decision rule, or may elect to remove the rule altogether, or may elect to maintain the rule without adjustment.

Having provided an overview of a monitoring device for monitoring a medical imaging device 2 with reference to FIG. 1, some additional embodiments and examples are presented in the following.

In regards to the processing operations 30, 32, there are different types of manuals associated with the medical imaging device 2 that provide a lot of information on the device. The user manual 27 can inform about features of the medical imaging device and how to use it, its use case bounding conditions, and this helps to determine correct practice and use by the user. The service manual 25 can give further detailed information at the component level, its life span based on use, absolute life, symptoms and behaviors, action needs to be taken for each problem and other critical parameters and their bounds. Similarly, manufacturer specifications 26 are an important element of cost and quality control for testing, calibration and other measurement processes. Integrating the information from the above manuals provides comprehensive information for providing maintenance alerts in furtherance of predictive maintenance for the medical imaging device and its components. Data ingested from the user manual 27, service manual 25, and the manufacturer specifications 26 are parsed to extract the context relevant information from the documents. The Component Entity Recognition (CER) 32 is performed to identify names of components (i.e. component IDs) and names of operating parameters so as to identify relevant operating parameters for these components. Co-reference is carried out to identify the specific sentence where the association is not clear. Dependency parsing is performed to identify the associated patterns to the specific components that needs to be mapped. Further, each of the relevant sentences associated with the components are extracted and tabulated.

Figure 2:
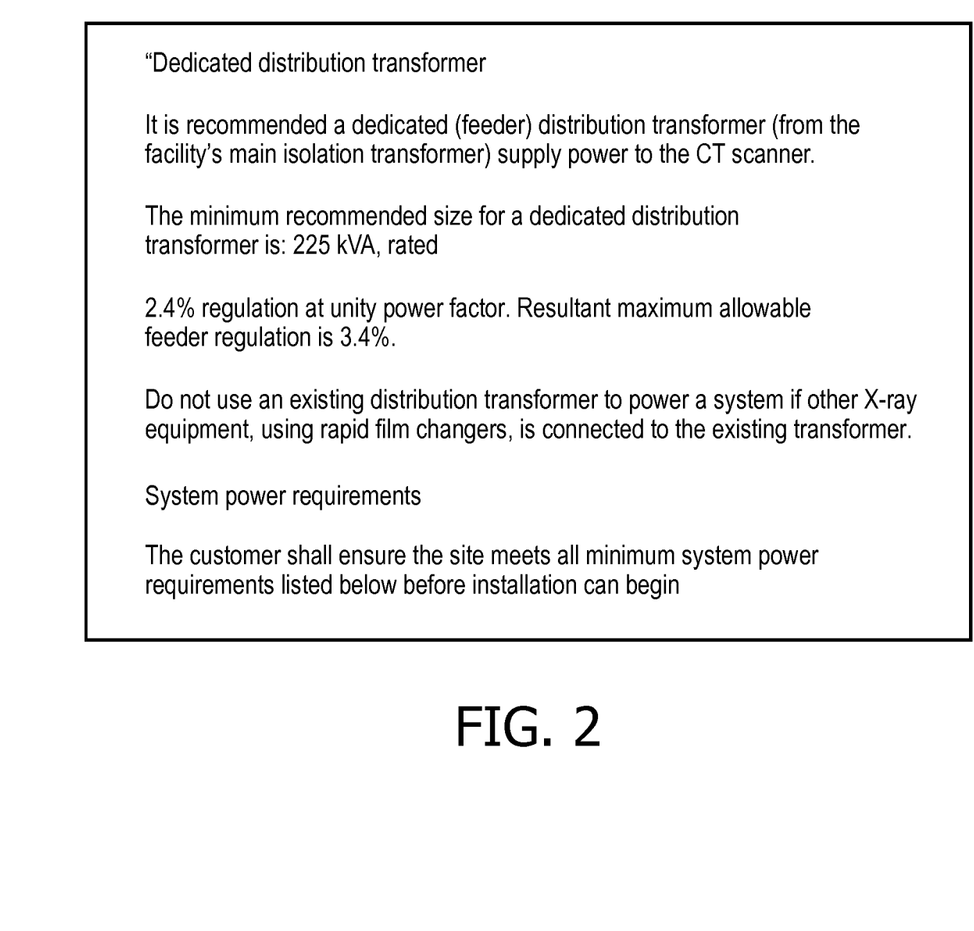
FIG. 2 diagrammatically illustrates a portion of a medical imaging device manual.
Figure 3:
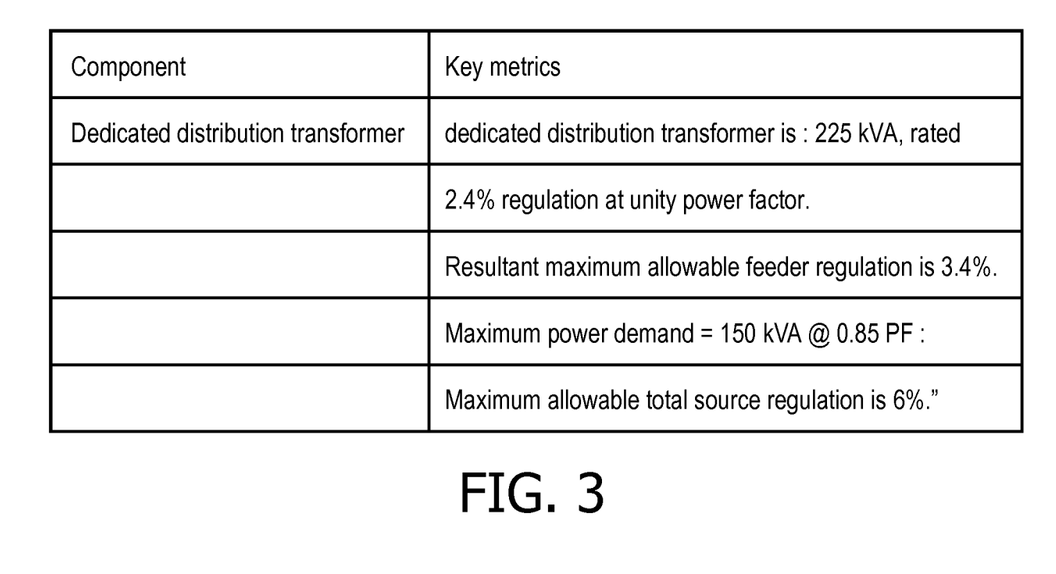
FIG. 3 diagrammatically illustrates a table of components and key metrics derived from the manual portion shown in FIG. 2.

With reference to FIGS. 2 and 3, an example is shown. FIG. 2 shows an example of manual content for a dedicated distribution transformer from a CT installation guide. FIG. 3 shows a component ID extracted from the content of FIG. 2, namely the component ID "Dedicated Distribution Transformer", and key metrics extracted for that component. All other extracted component IDs are similarly processed to arrive at a structured table (FIG. 3 being a portion of this table) containing all the components (or, more specifically, the component IDs) and the associated key metrics that needs to be monitored for the smooth running of the medical imaging device.

Figure 4:
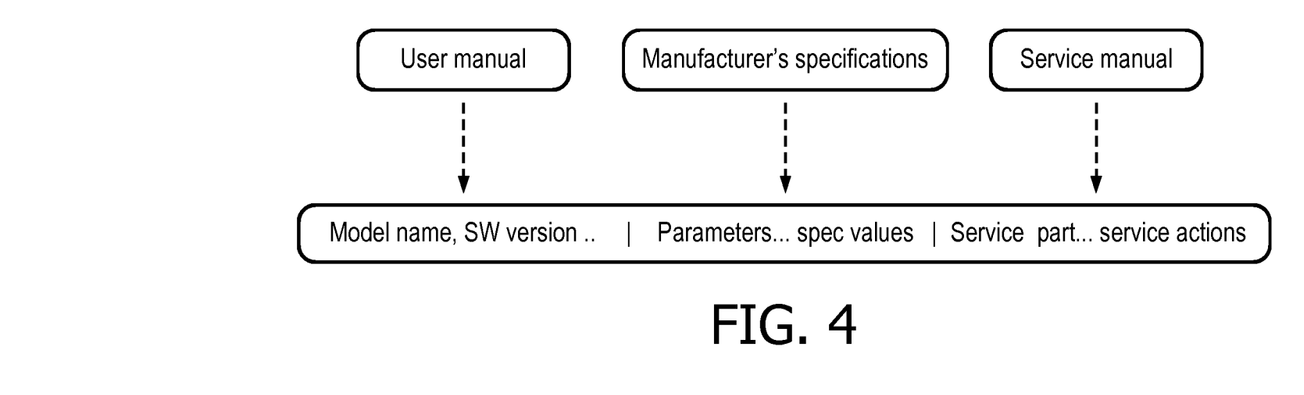
FIGS. 4, 5, and 6 diagrammatically illustrate aspects of generating the decision rules from medical imaging device manual content as described herein.

With reference now to FIG. 4, once the data has been extracted and the components table has been created, a composite is made that allows for the next step of data classification. The creation of the decision rules 36 of the knowledge engine 22 entails combining data extracted from the different manuals in a cogent way for every monitored component of the medical imaging device. For each component, from the vast inputs that were cleaned in the operations 30, 32, data from service manuals, manufacturer specifications, and user manuals are consolidated in the form of tables. This process is performed by: (1) Taking the system details from the user manuals such as system make, model etc. a unique ID can be associated with each system; (2) For the system details from step (1), the corresponding data from the manufacturer specifications are extracted and tagged with a unique key associated with the user manual, and (i) Once the system details are in place, using the service manual, the service actions pertaining to the specific system configurations are consolidated and tagged with the same unique ID. Once the above three steps are done, the data is tagged per system model. A mapping procedure is then performed, in which each of the faults that the system is known to suffer are extracted and mapped to the errors that a system logs and correlations are drawn from these to predict the nature of the data. This process is diagrammatically shown in FIG. 4.

Figure 5:
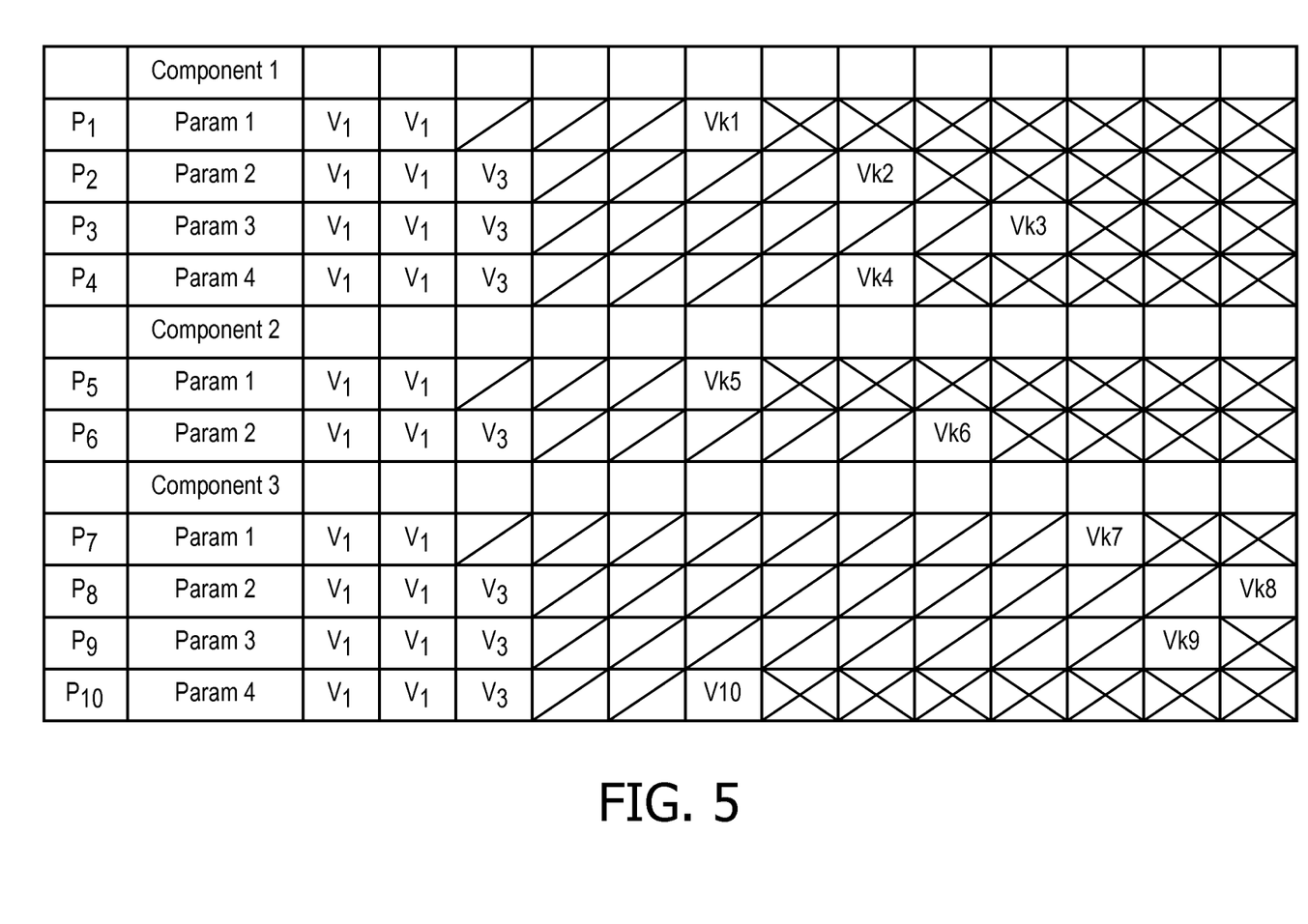

With reference to FIG. 5, the components and the operating parameters extracted for each component using the CER 32 with their possible values can be represented using a unstructured data table, as shown in FIG. 5. Let $P_1$, $P_2$, $P_3$, ..., $P_N$ be the N operating parameters extracted from the fixed number of components and let $Vk_1$, $Vk_2$, $Vk_3$, ..., $Vk_N$ represents possible parameter values for the respective components and parameters. These are the sets of parameters extracted from all the manuals using the NLP 30 and CER 32. The objective is to find meaningful combinations ($Ps_1$, $Ps_2$, $Ps_3$, ..., $Ps_M$, $M \leq N$) of these parameters and their respective optimal limits aiming to produce model a $M_c$ to produce good pool or bad pool based on each component. This can be explained notationally as given below:

$M_2 = YP_i$ is the set of rules based on only one parameter;
$M_2 = Y(P_{i_1}, P_{i_2})$ is the set of rules based on each combination of tuple;
$M_k = Y(P_{i_1}, P_{i_2}, ..., P_{i_k})$ is the set of rules based on k-tuple at a time;
Then
Let $$M_c = \psi_{l}^{N-1} (M_l)$$

be the models considering rules with optimal combination of all $M_k$.

Figure 6:
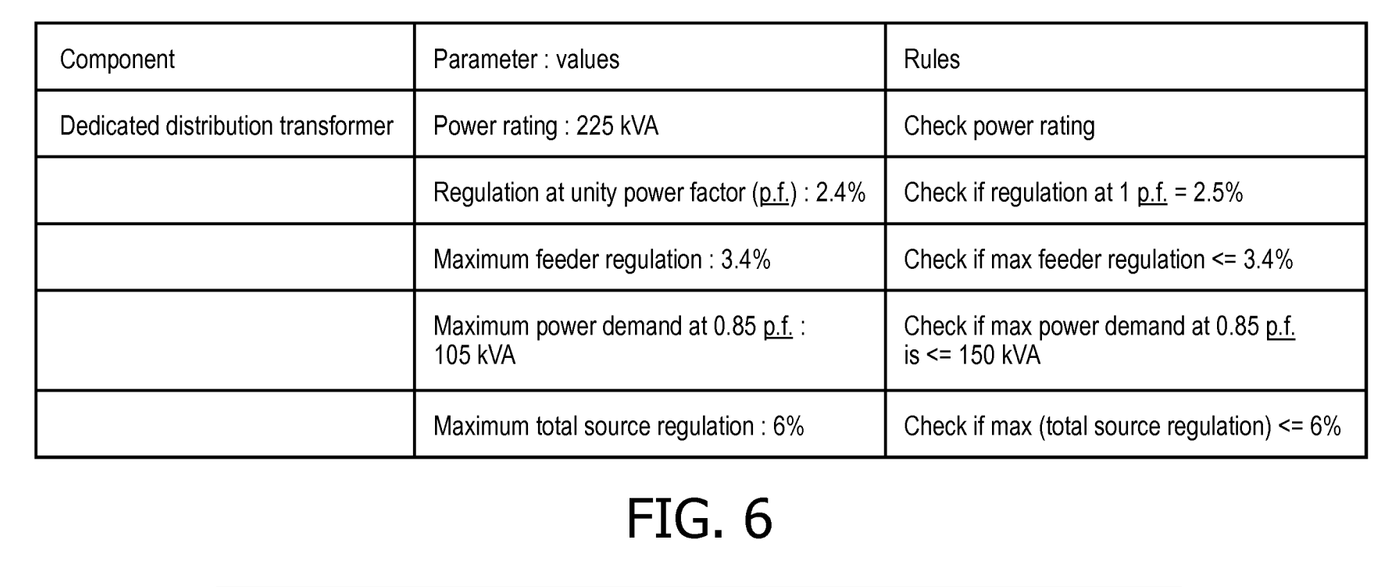

With reference to FIG. 6, the output of the resulting knowledge engine 22 will contain the set of decision rules 36 for each of the components as depicted in the sample table of FIG. 6, which aids in classifying the data into good and bad pool. Comparing FIG. 6 with FIG. 3 illustrates how the decision rules may be formulated as maintenance recommendations as shown in the rightmost column of FIG. 6.

In the following, some illustrative implementations of the ETL 42 and application of the knowledge engine 22 shown in FIG. 1 are described.

The process of mapping of the knowledge engine 22 with the machine log data 40 involves parsing of machine log data into system readable format and storing in database system, this process is the ETL 42 indicated in FIG. 1. The log data that is stored in database will be typically distributed in multiple tables of the database. The first step towards the goal of mapping of the knowledge engine 22 with the machine log 40 is to aggregate related log data from database. The log data can be related in two ways: (1) Temporal dependency of log information; and (2) shares a common component or sub-system.

Figure 7:
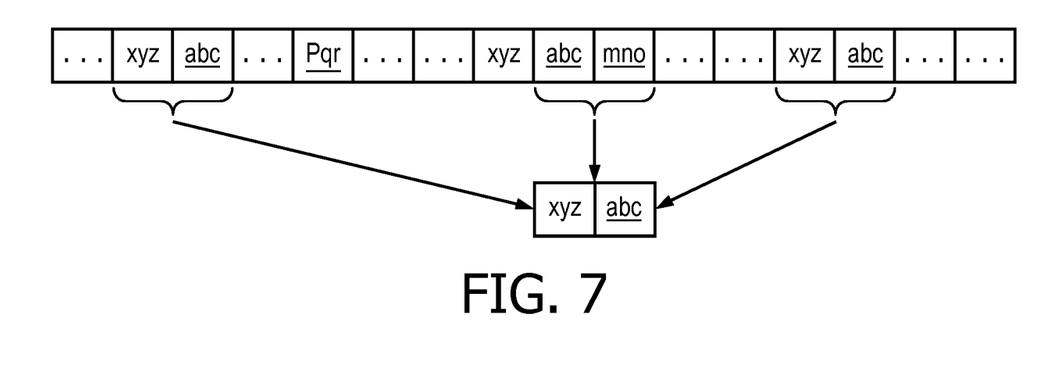
FIGS. 7 and 8 diagrammatically illustrate aspects of mapping of medical imaging device log data to decision rules of the knowledge engine as described herein.

With reference to FIG. 7, in the case of temporal dependency of log information, log data from databases is extracted and aligned in the temporal domain (increasing/decreasing) and temporal pattern-matching is used to extract dependent log information, e.g. as illustrated in FIG. 7.

The detection and aggregation of log information that belong to same type of component/sub-system can be performed using various approaches to detect correlating log data. One suitable approach is lexical analysis of content of log information and correlating lexical analysis output of two or more instances of log. A threshold on correlated value is used to categorize whether a given set of log information are related or not. Another illustrative approach is to count appearance or non-appearance of two or more error log data in given timeframe (typically data generated over a single day) and categorize as belong to same or different groups. Yet another illustrative approach is to compute mutual exclusivity of given set of log information with one another, two or more log information data having least mutual exclusive value will be considered as belong to same group of errors.

Figure 8:
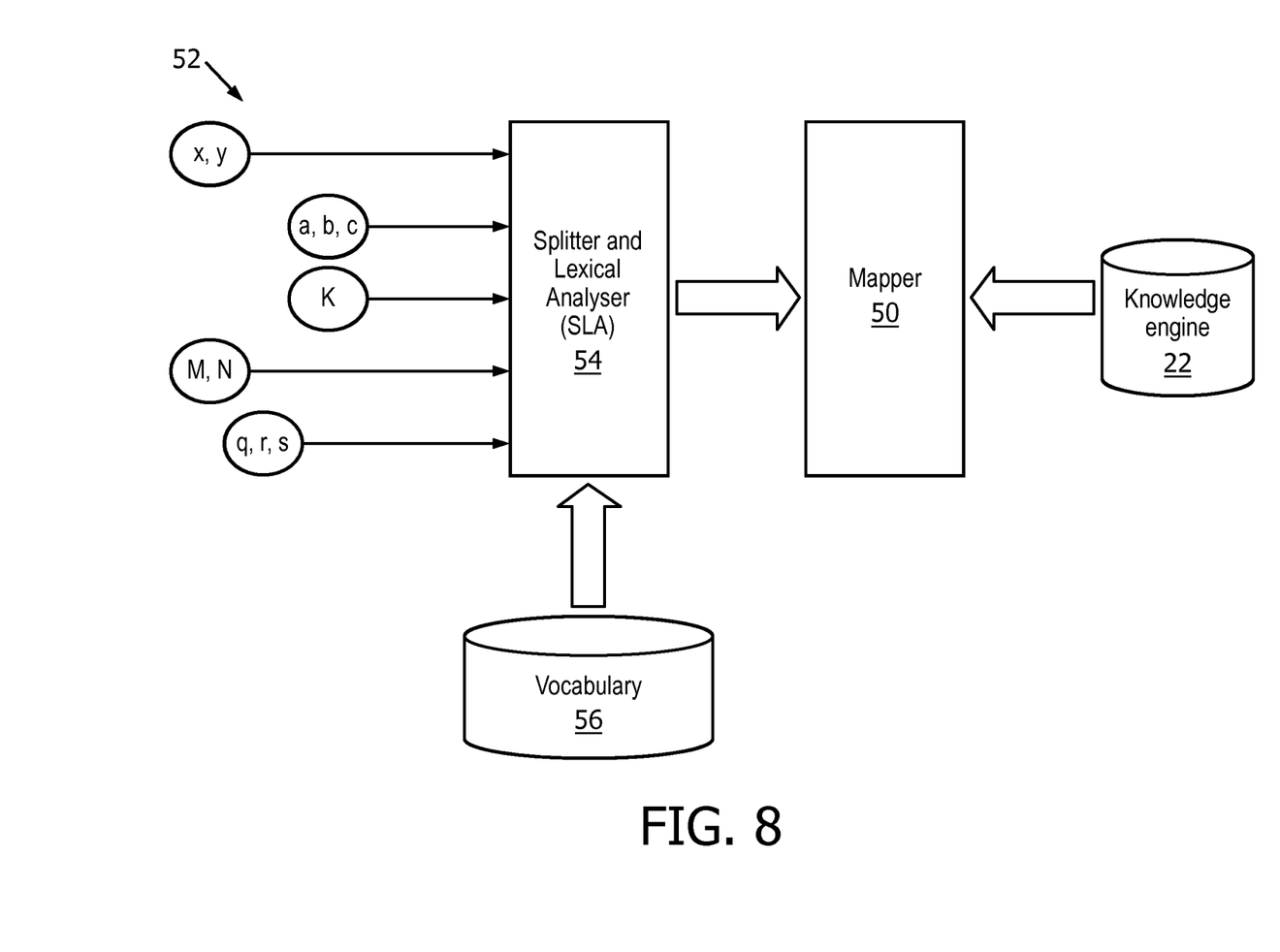

With reference to FIG. 8, once the log data is segregated into groups, the matching of system log data 40 with the knowledge engine 22 is performed. To perform mapping 50 of the log data, each group 52 of segregated log information is sent to a splitter and lexical analyzer (SLA) unit 54. The SLA unit 54 first splits log information into meaningful tokens (typically words) and then each token is cross-correlated with a set of vocabulary words 56 derived from source that generated knowledge engine (e.g. electronic medical imaging device servicing and operating data such as the illustrative user manual 27, specification data 26, service manual 25). Each element in the vocabulary 56 is assigned weight based on its importance. The weightage is decided by using domain expertise and/or by using statistical techniques like counting of words appearing in knowledge engine, number of connectivity of a given word with unique different works, etc. The vocabulary 56 is suitably derived from CER 32. The mapper 50 uses weighted and tokenized data from the SLA unit 54 to map log information with entries (e.g. decision rules) of the knowledge engine 22 as at this stage both type of data (log data and knowledge engine rules) will be of same nature as well as employing common language owing to fact that log data is processed using the stored vocabulary 56. The mapping 50 can be achieved by techniques such as word similarity matching or correlating the words.

Figure 9:
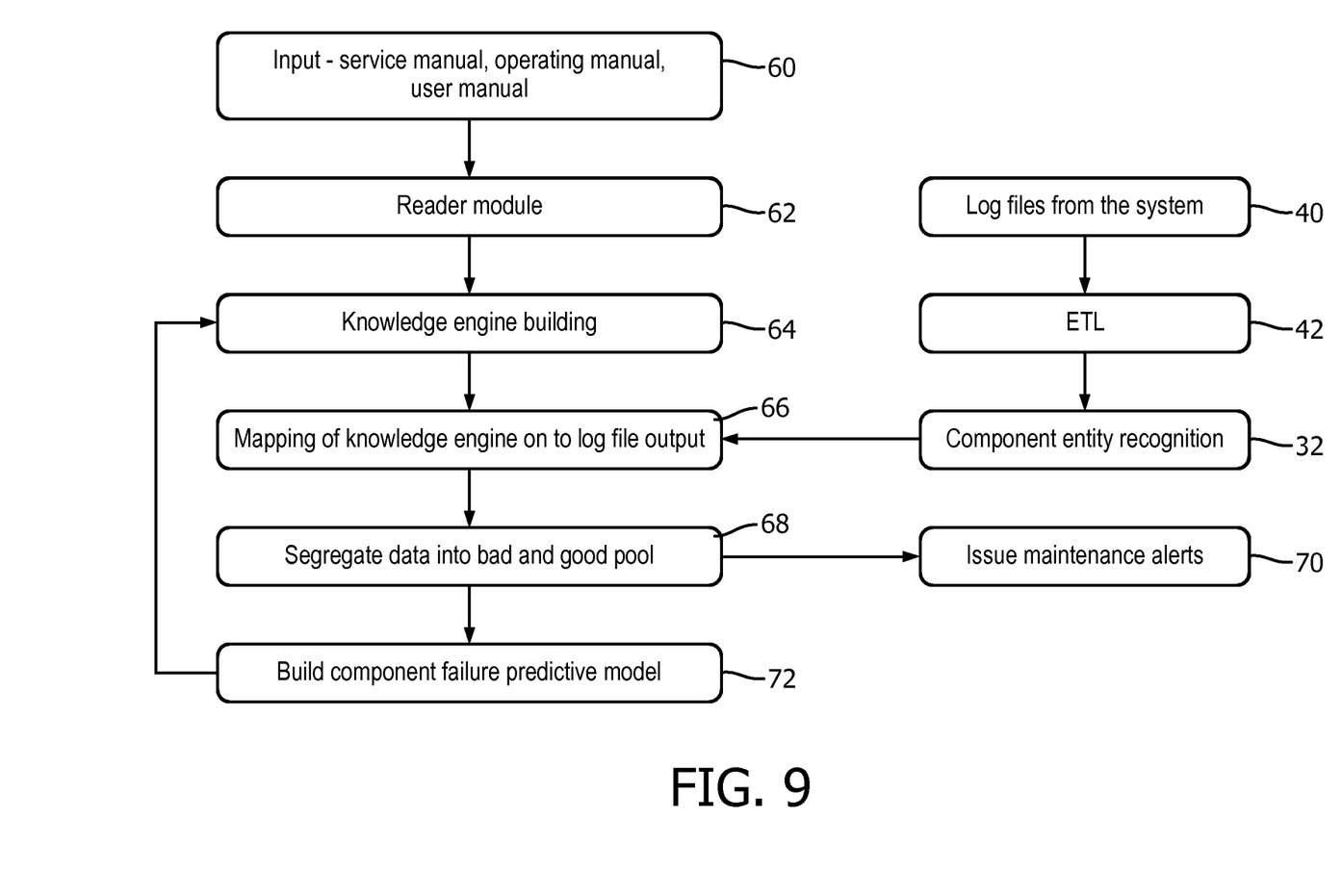
FIG. 9 diagrammatically illustrates a method suitably performed by the monitoring device of FIG. 1 to construct decision rules of the knowledge engine.

With reference to FIG. 9, a method suitably performed by the monitoring device of FIG. 1 to construct the decision rules 36 of the knowledge engine 22 is illustrated. In an operation 60, the various electronic medical imaging device servicing and operating data 25, 26, 27, 28 are input to the knowledge engine builder 20. In an operation 62, a reader module (e.g. illustrative NLP 30 and CER 32) is applied to extract component IDs and operating parameters from the manuals, as well as associated operating parameter ranges. In an operation 64, the knowledge engine 22 is built by operations including formulating the operating parameter ranges into the set of decision rules 36 for classifying medical imaging device log data as good or bad log data. As shown on the right-side of FIG. 9, during deployment of the knowledge engine 22, the log files 40 from the medical imaging device 2 are pre-processed by the ETL 42. The CER 32 is applied to the ETL-processed log data to extract component IDs and operating parameters and values thereof. This is suitably done by applying the same CER 32 used in processing the manuals to the ETL-processed log data. In an operation 66, the decision rules 36 of the knowledge engine 22 are mapped on the log file output by the ETL/CER processing chain. The operation 66 may be performed as already described with reference to FIG. 8. In an operation 68, the output of the mapping 66 is used to segregate log data into good data (in which the operating parameters are in range as defined by the decision rules 36) or bad data (in which at least one operating parameter is out of range as defined by the decision rules 36). In an operation 70, maintenance alerts 24 are issued based on detected bad data. In an optional adaptive updating operation 72, the bad data may be used to update the decision rules 36 based on whether the maintenances alerts are determined to be accurate (e.g., based on information from the service log 44 on whether the subject component was serviced or failed during the MTTF time interval after issuance of the maintenance alert).

Figure 10:
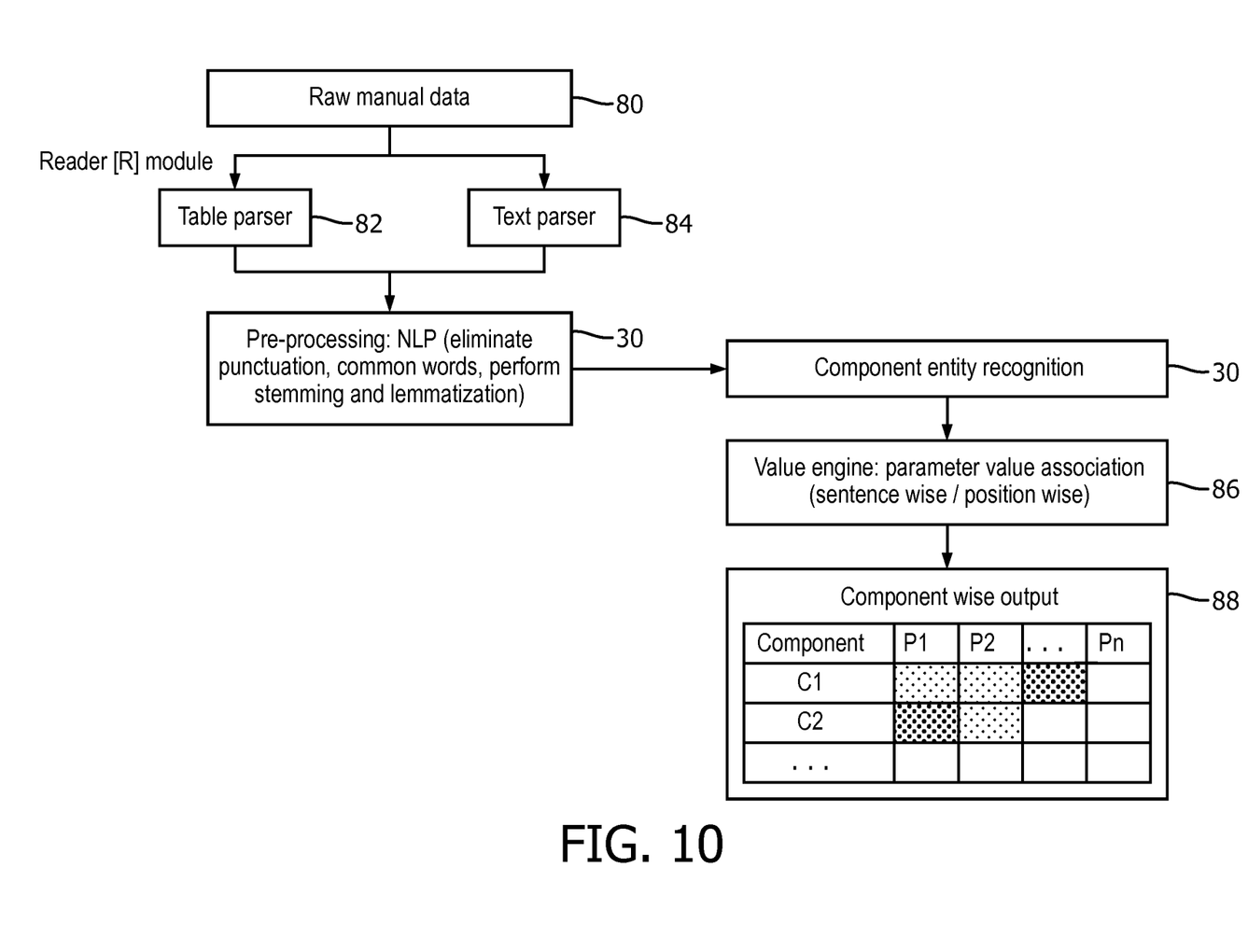
FIGS. 10 and 11 diagrammatically illustrate aspects of the reader module component of the method of FIG. 9.
Figure 11:
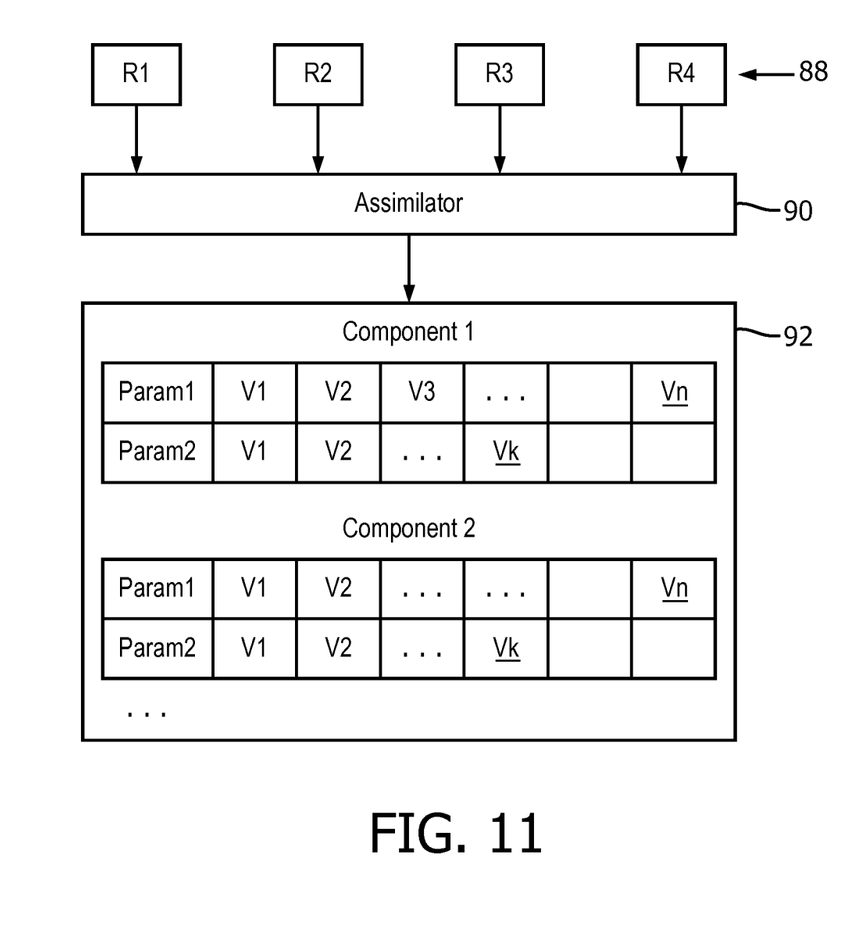

With reference to FIGS. 10 and 11, an illustrative more detailed implementation of the reading operation 62 (e.g. illustrative NLP 30 and CER 32) is described. Referencing FIG. 10, the textual content of the raw manual data 80 typically includes tables and text (e.g. paragraphs, sentences, bullet points, ordered lists, or so forth). A table parser 82 parses table content into semantic units such as rows and/or cells, while a text parser 84 parses textual content into semantic units such as sentences or paragraphs. The NLP 30 and CER 32 are then applied as previously described to extract component IDs and operating parameters and associated operating parameter ranges or values. In the example of FIG. 10, this latter processing is shown separately as a value engine component 86, where parameter value association is performed on a sentence-wise, cell-wise, or other semantic unit basis, to generate component-wise output 88. Turning to FIG. 11, the component-wise outputs 88 from the various electronic medical imaging device servicing and operating data 25, 26, 27, 28 are combined by an assimilator 90 to generate the combined unstructured data table 92, as already described with reference to FIG. 5. This data table 92 then serves as input to the knowledge engine building operation 64 of FIG. 9.

The invention has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A non-transitory storage medium storing instructions readable and executable by an electronic processor to perform a monitoring method for generating maintenance alerts, the monitoring method comprising:
extracting component identifications (component IDs) identifying medical imaging device components and operating parameters of the identified medical imaging device components and associated operating parameter ranges from electronic medical imaging device servicing and operating data;
generating a knowledge engine by operations including formulating the operating parameter ranges into a set of decision rules for classifying medical imaging device log data, wherein formulating the operating parameter ranges into the set of decision rules includes formulating decision rules that classify input log data as out-of-range log data if the input log data indicates a value for an operating parameter that is outside of the operating parameter range associated with that operating parameter; and
applying the knowledge engine to log data generated by a monitored medical imaging device to detect out-of-range log data generated by the monitored medical imaging device and to generate maintenance alerts in response to the detected out-of-range log data wherein the maintenance alerts are associated with component IDs contained in the detected out-of-range log data.

2. The non-transitory storage medium of claim 1 wherein the monitoring method further comprises:
determining accuracy of generated maintenance alerts based on feedback extracted from a service log of the monitored medical imaging device; and
updating the knowledge engine by adjusting the decision rules based on the determined accuracy of the generated maintenance alerts.

3. The non-transitory storage medium of claim 2 wherein the applying of the knowledge engine includes generating a maintenance alert in response to a detected combination of two or more parameters that are outside their respective operating parameter ranges in the out-of-range log data.

4. The non-transitory storage medium of claim 1 wherein the extracting of component IDs employs a named entity recognition (NER) algorithm.

5. The non-transitory storage medium of claim 4 wherein the extracting of operating parameters of the identified medical imaging device components and associated operating parameter ranges includes:
parsing text and tables of the electronic medical imaging device manuals to delineate semantic units including at least sentences, list items, and table rows or cells;
identifying operating parameters by identifying numeric values and parameter terms which are connected by linking terms or symbols indicative of equality or inequality and associating parameters identified by the parameter terms with medical imaging device components whose component IDs occur in the same semantic units as the parameter terms; and
determining operating parameter ranges associated with operating parameters based on the numeric values and the equalities or inequalities indicated by the linking terms or symbols.

6. The non-transitory storage medium of claim 1 wherein the generated maintenance alerts are formulated as maintenance recommendations and the monitoring method further includes controlling a display to present the maintenance recommendations in response to detected out-of-range log data.

7. The non-transitory storage medium of claim 1 wherein the extracting is performed on electronic medical imaging device servicing and operating data including at least one electronic medical imaging device manual.

8. A monitoring device for generating maintenance alerts, the monitoring device comprising:
a display;
a non transitory storage medium readable and executable by an electronic processor to perform a monitoring method for generating maintenance alerts as set forth in claim 1; and an electronic processor operatively connected with the display and with the non transitory storage medium to perform the monitoring method further including displaying the generated maintenance alerts on the display.

9. A monitoring method for generating maintenance alerts, the monitoring method comprising:
by an electronic processor, extracting component identifications (component IDs) identifying medical imaging device components in electronic medical imaging device manuals;
by the electronic processor, extracting operating parameters of the identified medical imaging device components and associated operating parameter ranges from the electronic medical imaging device manuals based on numeric values, parameter terms identifying operating parameters, and linking terms or symbols indicative of equality or inequality that connect the numeric values and parameter terms;
by the electronic processor, formulating the operating parameter ranges into decision rules for classifying medical imaging device log data based on whether a value of the associated operating parameter is outside of the operating parameter range, wherein the maintenance alerts are formulated as recommendations to check the value of the operating parameter associated with the operating parameter range of the decision rule that produced the maintenance alert; and
by the electronic processor, applying the decision rules to log data generated by a monitored medical imaging device to detect out-of-range log data generated by the monitored medical imaging device; and
displaying maintenance alerts on a display in response to the detected out-of-range log data wherein the maintenance alerts are generated from out-of-range log data and are associated with component IDs contained in the out-of-range log data.

10. The monitoring method of claim 9 wherein the monitoring method further comprises:
by the electronic processor, determining accuracy of maintenance alerts based on feedback extracted from a service log of the monitored medical imaging device; and
updating the decision rules based on the determined accuracy.

11. The monitoring method of claim 9 wherein the applying of the decision rules to detect out-of-range log data includes applying a decision rule to detect a combination of two or more parameters that are outside their respective operating parameter ranges in the out-of-range log data.

12. The monitoring method of claim 9 wherein the extracting is performed on electronic medical imaging device manuals including at least one of a user manual or an operating reference manual.

13. A monitoring device for generating maintenance alerts, the monitoring device comprising:
a display;
an electronic processor operatively connected with the display; and
a non-transitory storage medium storing instructions readable and executable by the electronic processor to perform a monitoring method for generating maintenance alerts, the monitoring method comprising:
generating decision rules for classifying medical imaging device log data based on whether parameter values of operating parameters of medical imaging device components identified by component identifications (component IDs) in the log data are within operating parameter ranges for the respective operating parameters wherein the operating parameter ranges for the respective operating parameters are extracted from electronic medical imaging device manuals;
applying the decision rules to log data generated by a monitored medical imaging device to detect out-of-range log data generated by the monitored medical imaging device;
controlling the display to present maintenance alerts in response to the detected out-of-range log data wherein the maintenance alerts are associated with component IDs contained in the detected out-of-range log data;
determining accuracy of the presented maintenance alerts based on feedback extracted from a service log of the monitored medical imaging device; and
updating the decision rules based on the determined accuracy of the presented maintenance alerts;
wherein at least one of:
(i) accuracy of a presented maintenance alert is determined based on feedback extracted from the service log of the monitored medical imaging device over a time interval extending from a time of presentation of the maintenance alert to an end time dependent upon a mean time to failure (MTTF) of the medical imaging device component identified by the component ID associated with the maintenance alert; and/or
(ii) the generating of the decision rules further includes parsing text and tables of the electronic medical imaging device manuals to delineate semantic units including at least sentences, list items, and table rows, identifying operating parameters by identifying numeric values and parameter terms that are connected by linking terms or symbols indicative of equality or inequality and associating operating parameters identified by the parameter terms with medical imaging device components whose component IDs occur in the same semantic units as the parameter terms, and determining operating parameter ranges associated with the identified operating parameters based on the numeric values and the equalities or inequalities indicated by the linking terms or symbols.

14. The monitoring device of claim 13 wherein accuracy of a presented maintenance alert is determined based on feedback extracted from the service log of the monitored medical imaging device over a time interval extending from a time of presentation of the maintenance alert to an end time dependent upon a mean time to failure (MTTF) of the medical imaging device component identified by the component ID associated with the maintenance alert.

15. The monitoring device of claim 13 wherein the generating of the decision rules includes identifying the component IDs in the medical imaging device manuals using a named entity recognition (NER) algorithm.

16. The monitoring device of claim 15 wherein the generating of the decision rules further includes:
parsing text and tables of the electronic medical imaging device manuals to delineate semantic units including at least sentences, list items, and table rows;
identifying operating parameters by identifying numeric values and parameter terms that are connected by linking terms or symbols indicative of equality or inequality and associating operating parameters identified by the parameter terms with medical imaging device components whose component IDs occur in the same semantic units as the parameter terms; and determining operating parameter ranges associated with the identified operating parameters based on the numeric values and the equalities or inequalities indicated by the linking terms or symbols.

17. The monitoring device of claim 13 wherein the presented maintenance alerts are presented as maintenance recommendations.

* * * * *